United States Patent [19]
Thorner et al.

[11] Patent Number: 5,973,114
[45] Date of Patent: Oct. 26, 1999

[54] ISOLATION AND CHARACTERIZATION OF THE GROWTH HORMONE RELEASING HORMONE RECEPTOR

[75] Inventors: Michael Oliver Thorner, North Garden; Bruce David Gaylinn, Trevilians, both of Va.; John Ronald Zysk, French Town, N.J.; Cecil Mark Eppler, Langhorne, Pa.

[73] Assignees: The University of Virginia Patent Foundation, Charlottesville, Va.; American Cyanamid Company, Wayne, N.J.

[21] Appl. No.: 07/902,826

[22] Filed: Jun. 23, 1992

[51] Int. Cl.⁶ .................................................. C07K 14/705
[52] U.S. Cl. .......................... 530/350; 530/395; 530/399; 530/412
[58] Field of Search .................................... 530/399, 350, 530/412, 395

[56] References Cited

U.S. PATENT DOCUMENTS 4,833,166  5/1989  Grosvenor et al. .

FOREIGN PATENT DOCUMENTS

WO 92/00095  1/1992  European Pat. Off. .
0 506 032 A1  9/1992  European Pat. Off. .

OTHER PUBLICATIONS

Zysk et al., "Cross–Linking of a Growth Horomone Releasing Factor–Binding Protein in Anterior Pituitary Cells," *J. Biol. Chem.*, 261: 16781–16784 (1986).

Velicelebi et al., "Covalent Cross–Linking of Growth Hormone–Releasing Factor to Pituitary Receptors," *Endocrinology*, 118: 1278–1283 (1986).

Struthers et al., "Nucleotide Regulation of Growth Hormone–Releasing Factor Binding to Rat Pituitary Receptors," *Endocrinology*, 124: 24–29 (1989).

Christophe et al., "The VIP/PHI/Secretin–Helodermin/Helospectin/GRF Family: Structure–Function Relationship of the Natural Peptides, Their Precursors and Synthetic Analogs as Tested in vitro on Receptors Adenylate Cyclase in a Panel of Tissue Membranes," *Peptide Hormones As Prohormones: Processing, Biological Activity, Pharmacology*, Ed. Jena Martinez, Publ. Ellis Horwood Lim, Chichester, England (1989).

Laburthe et al., "Molecular Analysis of Vasoactive Intestinal Peptide Receptors: A Comparison With Receptors for VIP–Related Peptides," *Ann. NY Acad. Sci.*, 527: 296–313 (1988).

Froham et al., "Growth Hormone–Releasing Hormone," *Endocr Rev.*, 7: 223–253 (1986).

Seifert et al., "Growth Hormone–Releasing Factor Binding Sites In Rat Anterior Pituitary Membrane Homogenates: Modulation By Glucocorticoids," *Endocrinology*, 117: 424–426 (1985).

Bilezikjian et al., "Desensitization To Growth Hormone–Releasing Factor (GRF) Is Associated With Down–Regulation of GRF–Binding Sites," *Endocrinology*, 118: 2045–2052 (1986).

Ishihara et al., "Functional Expression and Tissue Distribution of a Novel Receptor for Vasoactive Intestinal Polypeptide," *Neuron*, 8:811–819 (1992).

Ishihara et al., "Molecular Cloning and Expression of a cDNA Encoding the Secretin Receptor," *EMBO J*, 10:1635–1641 (1991).

Lin, et al., "Expression Cloning of an Adenylate Cyclase–Coupled Calcitonin Receptor," *Science*, 254:1022–1024 (1991).

Juppner, et al., "A G Protein–Linked Receptor For Parathtroid Hormone and Parathyroid Hormone–Related Peptide," *Science*, 254:1024–1026 (1991).

Frohman, et al., Tissue Distribution and Molecular Heterogeneity of Human Growth Hormone–Releasing Factor in the Transgenic mouse, *Endocrinology*, 127:2149–2156 (1990).

Paul et al., "Characterization of Receptors for Vasoactive Intestinal Peptide Solubilized From the Lung," *J. Biol. Chem.*, 262:158–162 (1987).

Guijarro et al., "Solubilization of Active and Stable Receptors for Vasoactive Intestinal Peptide from Rat Liver," *Regulatory Peptides*, 25:37–50 (1989).

Cronin et al., "Biological Activity of a Growth Horomone Releasing Factor Secreted By A Human Tumor," *Am. J. Physiol.*, 244 (Endocrinol Metab) E346–E353 (1983).

Leong et al., "Enumeration of Lactotropes and Somatotropes in Cultured Male and Female Pituitary Cells: Evidence in Favor of a Mammosomatotrope Subpopulation in the Rat," *Endocrinology*, 116:1371–1378 (1985).

Munson et al., "Ligand: a Versatile Computerized Approach For Characterization of Ligand–Binding Systems," *Anal. Biochem.*, 107:220–239 (1980).

Wessel, et al., "A Methodo for the Quantitative Recovery of Protein in Dilute Solution in the Presence of Detergents and Lipids," *Anal. Biochem.*, 138:141–143 (1984).

Bagnato et al., Gonadotropin–Induced Expression of Receptors for Growth Hormone Releasing Factor in Cultured Granulosa Cells*, *Endocrinology*, 128:2889–2894 (1991).

(List continued on next page.)

*Primary Examiner*—Sally P. Teng
*Attorney, Agent, or Firm*—Burns, Doane, Swecker & Mathis, L.L.P.

[57] ABSTRACT

Growth hormone releasing hormone (GHRH) receptor binding has been characterized using a unique binding assay utilizing iodinated GHRH probes. Photoaffinity GHRH probes have been constructed which allow for photolabeling and characterization of the receptor. In addition, high affinity biotinylated GHRH analogs have been constructed. Solubilization of GHRH-R/GHRH complexes and extraction of specifically bound GHRH using a mild detergent solution, followed by affinity chromotography, leads to a substantially purified GHRH-R isolate. Electrophoretic treatment of the GHRH-R isolate produces GHRH-R of sufficient purity to conduct sequencing of the receptor.

9 Claims, 9 Drawing Sheets

OTHER PUBLICATIONS

Ikuyama et al., "Characterization of Growth Hormone–Releasing Hormone Receptors in Pituitary Adenomas from Patients with Acromegaly," *J. Clinical Endocrinology and Metabolism* 66:1265–1271 (1988).

Gaylinn et al., "Photoaffinity Crosslinking to GHRH–Receptor Followed by Cyanogen Bromide Cleaviage Produces a labeled 12 kD Glycosylated Peptide," Abstract presented at the Endocrine Society Meeting, Jul. 1993.

Zysk et al., "Purification of the Receptor for Growth Hormone by Streptavidin Sepharose Chromatography," Abstract presented at the Endocrine Society Meeting, Jul. 1993.

Gaylinn et al., "Molecular Cloning and Expression of a Human Anterior Pituitary Receptor for Growth Homrone–Releasing Hormone," *Molecular Endocrinology,* 7:77–84 (1993).

Kelly E. Mayo, "Molecular Cloning and Expression of a Pituitary–Specific Receptor for Growth Hormone–Releasing Hormone," *Molecular Endocrinology,* 6:1734–1744 (1992).

Lin et al., "Pit–1–dependent expression of the receptor for growth hormone releasing factor mediates pituitary cell growth," *Nature* 360:765–768 (Dec. 1992).

Seifert et al., "Binding Sites for Growth Hormone Releasing Factor on Rat Anterior Pituitary Cells," *Nature* 313:487–489 (Feb. 1985).

Day et al., "Expressionof an antisense viral gene in transgenic tobacco confers resistance to the DNA virus tomato golden mosaic virus," *Proc. Natl. Acad. Sci. USA,* 88:6721–6725 (Aug. 1991).

Szczylik et al., "Selective inihibition of Leukemia Cell Proliferation by BCR–ABL Antisense Oligodeoxynucleotides," *Science* 253:562–565 (Aug. 1991).

Han et al., "Inhibition of Moloney murine leukemia virus–induced leukemia in transgenic mice expressing antisense RNA complementary to the retroviral packaging sequences," *Proc. Natl. Acad. Sci. USA,* 88:4313–3417 (May 1991).

Zhang et al., "Radioimmunoassay of growth hormone–releasing hormone (GHRH) with a polyclonal antibody against synthetic GHRH (1–29)–Gly$_4$–Cys–NH$_2$: method and clinical studies," *Clinica Chimica Acta,* 202:243–254 (1991).

Thomas et al., 1990, Methods in Enzymology, 182, 499–520.

Masu et al., 1987, Nature, 329, 836–836.

Yoshida et al., Neuroendocrinology, vol. 52 (51), p. 133, No. P3.106, 1990.

Gearing et al., Embo J., v.8, p. 3667, 1987.

Libert et al., Science, v.244, p. 569, 1989.

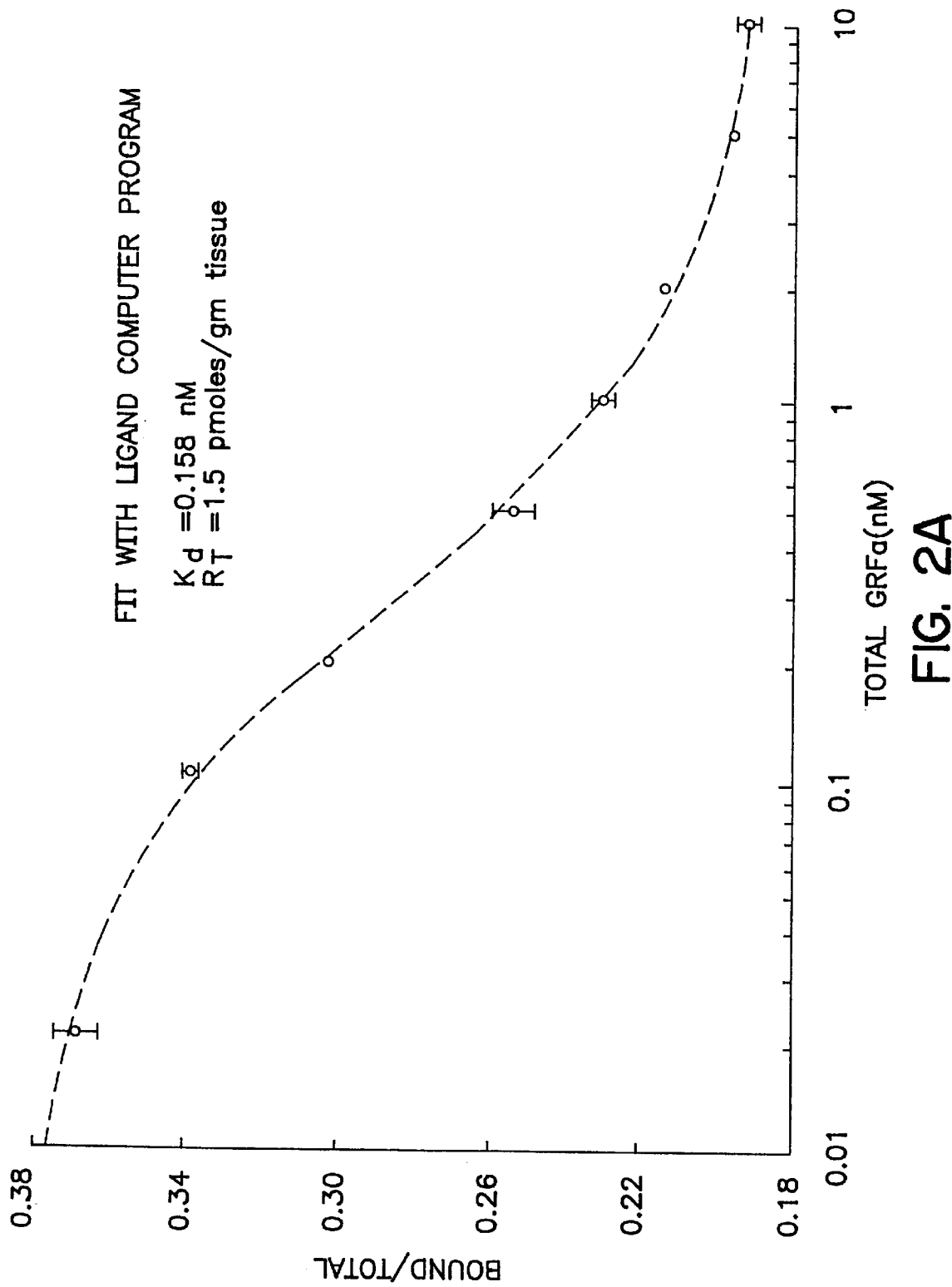

Deglycosylation of Photo-affinity Crosslinked Receptor

Photoaffinity Crosslinking with Deglycosylation

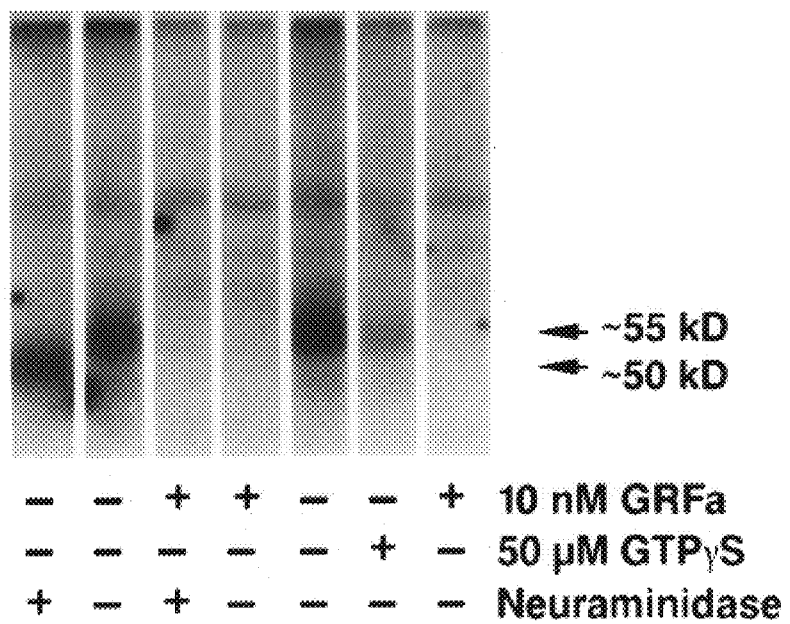
FIG. 5 Photoaffinity Crosslinking with Desialylation 10/25/91
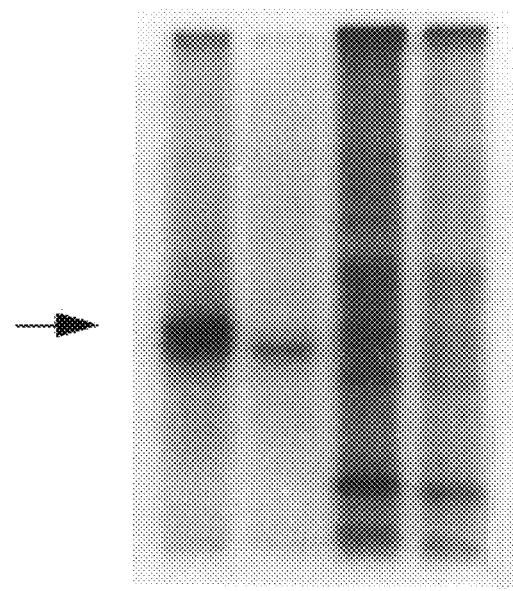
FIG. 7 Photoaffinity Crosslinking of Soluble Complexes 7/30/91

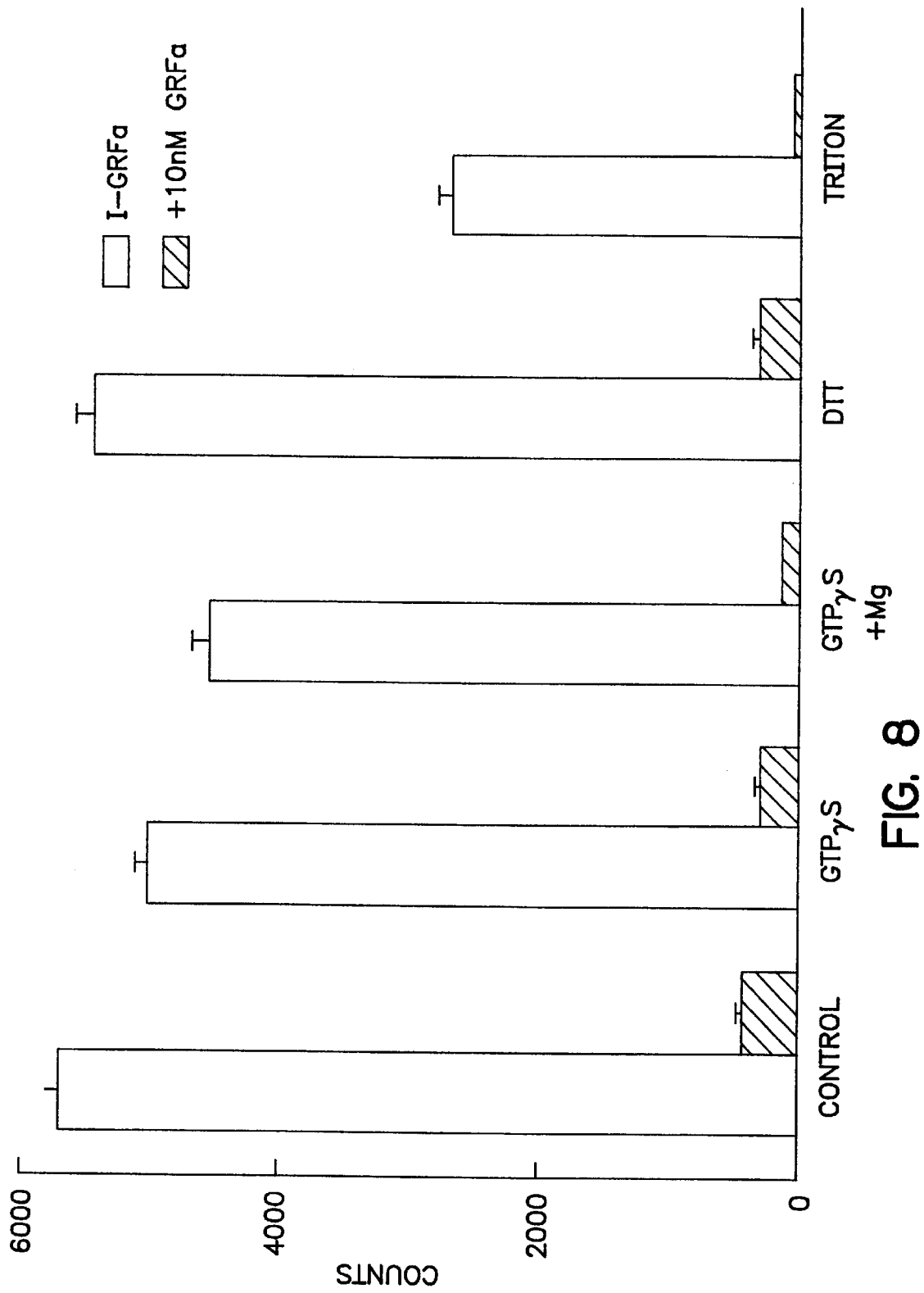

ISOLATION AND CHARACTERIZATION OF THE GROWTH HORMONE RELEASING HORMONE RECEPTOR

STATEMENT AS TO RIGHTS TO INVENTIONS MADE UNDER FEDERALLY-SPONSORED RESEARCH AND DEVELOPMENT

This invention was made with government support under DK32632 grant awarded by the National Institutes of Health. The Government has certain rights in the invention.

FIELD OF THE INVENTION

This invention is directed to isolation and characterization of hormone receptors, and is directed more particularly to methods and compositions useful in purifying and characterizing the growth hormone releasing hormone receptor, and to isolation of purified growth hormone releasing hormone receptor.

BACKGROUND OF THE INVENTION

Growth hormone releasing hormone (GHRH) is secreted by the hypothalamus, and stimulates the release of growth hormone (GH) from the anterior pituitary. GHRH is a member of a family of homologous peptides that includes glucagon, secretin, VIP (vasoactive intestinal peptide), PHI (peptide histidine isoleucine), PACAP (pituitary adenylate cyclase activating peptide), GIP (gastric inhibitory peptide), and helodermin. GHRH has been the subject of considerable study, but little is known about the GHRH receptor, GHRH-R, to which GHRH binds in the anterior pituitary to induce the release of GH.

Large scale production of the cloned GHRH receptor would enable the screening of large numbers of GHRH analogs, and would facilitate the development of improved agonists and antagonists in the clinical therapy of growth disorders. More specifically, the screening of large numbers of analogs and xenobiotics for GHRH activity could lead to the development of improved agonists for use in clinical therapy of growth hormone deficient children, and in clinical therapy of adults to improve nutrition and to alter body composition (muscle vs. fat). Such screening, possibly assisted by computer modeling based on receptor structure, could also lead to orally active non-peptide GHRH agonists that would be especially useful in medical and veterinary practice, for example, to develop higher yield milk production and higher yield, leaner livestock.

Commerical exploitation of drugs which interact with the GHRH-R will require a source of a purified form of GHRH-R and suitable binding assays.

The isolation and cloning of the GHRH receptor and its in vitro expression will also lead to: (1) In situ hybridization studies mapping the distribution of GHRH receptors throughout the body and to examination of their potential physiological role outside the pituitary; this might reveal potential roles for GHRH in the brain, gonad, pancreas, placenta, and gut, where the peptide is thought to be concentrated. (2) Studies of receptor structure involving mutated or chimeric receptors to explore structure/function relations and second messenger interactions in the quest for specifically tailored agonist/antagonist molecules. (3) An understanding of the GHRH-R's evolutionary relation to other G-protein-linked receptors, especially those in the glucagon/secretin/VIP family. (4) Cloning of other members of this sub-family that are expected to have sequence similarity.

There are several alternate routes towards obtaining functional receptor clones, such as: A. Purification of the receptor protein to obtain a partial protein sequence; this partial protein sequence could then be used to screen appropriate DNA for the corresponding nucleotide sequence. B. screening DNA for sequences similar to known receptors thought to be related to the GHRH receptor. C. Screening for DNA that, when expressed as protein, yields GHRH receptor, which would be detected by GHRH binding, biological activity, or by a GHRH receptor antibody. Note that any conceivable cloning method requires binding assays as well as functional assays with GHRH and related peptides in order to identify the GHRH receptor and to characterize expressed clones.

There is thus a need for GHRH binding assays and compositions for use therein which will help characterize and isolate the GHRH receptor. In particular, there is a need for methods which can characterize the pituitary GHRH receptor in terms of size, glycosylation, solubility and stability of the receptor (GHRH-R)—ligand (GHRH or GHRH analog) complex, so that methods can be developed to purify the receptor protein and identify receptor clones. There is also a need for purified or partially purified GHRH-R and methods for obtaining same. By partially purified GHRH-R, it is meant that a GHRH-R isolate is formed having GHRH-R isolated from most of the organic matrix of the anterior pituitary cells. The GHRH-R isolate has a purity sufficient to allow for determining the GHRH-R sequence, with it being understood that this may require further purification to remove any remaining compounds which would interfere with sequencing, such as G-proteins. Nevertheless, the GHRH-R isolate of the present invention, produced using the extraction and isolation method of the present invention contains GHRH-R, preferably at a concentration greater than that at which GHRH-R is naturally present in the anterior pituitary, and the GHRH-R isolate can be further purified, if necessary, using SDS-PAGE to remove any compounds which would interfere with sequencing of the GHRH-R. Thus, the present invention also includes the production of GHRH-R of sufficient purity to conduct sequencing, or for use in bioassays of GHRH-R binding activity.

Historically the GHRH-R has been difficult to work with since GHRH has very high non-specific binding (making it difficult to determine whether or not GHRH or GHRH analogs are binding specifically to GHRH-R), and GHRH-R has extremely low abundance. The nonspecific binding of GHRH analogs to glass and plasticware has been a major problem in previous work limiting the accuracy and reproducibility of receptor binding studies. Because of the "sticky" nature of the negatively charged GHRH peptide, the use of a simple filtration type binding assay has been impossible. Nonspecific counts are so high as to preclude detection of specific binding. In addition, the commonly used blocking agent polyethylenimine, which is used for blocking nonspecific binding of proteins on glass fiber filters is positively charged, and will bind GHRH analogs (negatively charged) nonspecifically. Further, a soluble receptor preparation with high binding affinity, which would vastly enhance efforts to purify the GHRH-R, has not been available.

Prior studies have characterized the GHRH receptor with respect to it's affinity for probes, such as GHRH and related peptides, and linkage to G-protein. Attempts have also been made to use non-specific chemical cross-linkers to label the GHRH receptor. See, for example, Zysk, et al., "Cross-Linking of a Growth Hormone Releasing Factor-Binding Protein in Anterior Pituitary Cells," *J. Biol. Chem.,* 261:1678 (1986), and Velicelebi, et al., "Covalent Cross-Linking of Growth Hormone-Releasing Factor to Pituitary Receptors," *Endocrinology,* 118:1278 (1986). The results of these two studies suggest, respectively, the presence of a 26 KDa and a 70 KDa GHRH-receptor in the anterior pituitary. The discrepancy between the molecular weight found in these two studies emphasizes the difficulties involved in isolating and characterizing the GHRH-R, and the need for improved methods and compositions useful for isolating and characterizing the GHRH-R.

GHRH binding to the rat anterior pituitary is believed to be influenced by GTP, which causes the GHRH-receptor to reduce its affinity for GHRH (GTP is said to uncouple the G protein GHRH-receptor complex). The high affinity state of GHRH-R bound to GHRH is believed to be stabilized by interactions with a guanine nucleotide regulatory protein to form a hormone-receptor-G-protein ternary complex. GTP is hypothesized to destabilize the G-protein-receptor interactions, resulting in dissociation of the GHRH/GHRH-R-G-protein complex and reversion of the independent receptor to a low affinity state, while the liberated G-protein goes on to activate its respective second messenger system. See Struthers, et al., "Nucleotide Regulation of Growth Hormone-Releasing Factor Binding to Rat Pituitary Receptors," *Endocrinology,* 124:24–29 (1989).

It has been discovered that, in ovine and bovine anterior pituitary tissues, GHRH and its analogs are displaced by 500 to 1,000 fold lower concentrations of GHRHa than VIP or PACAP. This finding is complementary to binding properties noted in the human pancreas (a source of secretin and VIP receptors) where the ability to stimulate adenylate cyclase in the presence of GTP shows an order of potency of secretin>helodermin>PHI≧VIP>GHRH(1–27)NH$_2$. Similarly, using $^{125}$I-secretin, Kds obtained were secretin 0.8 nM, helodermin 200 nM, PHI 250 nM. VIP and GHRH (1–29)-NH$_2$ induce only 20% inhibition at 10 $\mu$M.

At supraphysiologic doses, GHRH is known to act at VIP receptors, and conversely VIP is a weak GHRH agonist.

Other articles which provide background information on isolation and characterization of hormone receptors include: Christophe, et al., "The VIP/PHI/secretin-helodermin/helospectin/GRH Family: Structure-Function Relationship Of The Natural Peptides, Their Precursors And Synthetic Analogs As Tested in vitro On Receptors And Adenylate Cyclase In A Panel Of Tissue Membranes," in *Peptide Hormones As Prohormones: Processing, Biological Activity, Pharmacology,* Ed. Jean Martinez, Pub. Ellis Horwood Lim. 1989, Chichester, England. Baburthe, et al., "Molecular Analysis of Vasoactive Intestinal Peptide Receptors: A Comparison With Receptors for VIP Related Peptides," *Ann NY Acad. Sci.,* 527:296–313 (1988). Frohm, et al., "Growth Hormone-Releasing Hormone," *Endocr Rev.,* 7:223–253 (1986). Seifert, et al., "Growth Hormone-Releasing Factor Binding Sites In Rat Anterior Pituitary Membrane Homogenates: Modulation By Glucocorticoids," *Endocrinolgy,* 117:424–426 (1985). Bilezikjian, et al., "Desensitization To Growth Hormone-Releasing Factor (GRF) Is Associated With Down-Reguolation of GRF-Binding Sites," *Endocrinology,* 118:2045–2052 (1986). Ishihara, et al., "Functional Expression and Tissue Distribution of a Novel Receptor for Vasoactive Intestinal Polypeptide," *Neuron,* 8:811–819 (1992). Ishihara, et al., "Molecular Cloning and Expression of a cDNA Encoding the Secretin Receptor," *EMBO J,* 10:1635–1641 (1991). Lin, et al., "Expression Cloning of an Adenylate Cyclase-Coupled Calcitonin Receptor," *Science,* 254:1022–1024 (1991). Juppner, et al., "A G Protein-Linked Receptor For Parathyroid Hormone and Parathyroid Hormone-Related Peptide," *Science,* 254:1024–1026 (1991). Frohman, et al., "Tissue Distribution and Molecular Heterogeneity of Human Growth Hormone-Releasing Factor in the Transgenic mouse," *Endocrinology,* 127:2149–2156 (1990). Paul et al., "Characterization of Receptors for Vasoactive Intestinal Peptide Solubilized From the Lung," *J. Biol. Chem.,* 262:158–162 (1987). Guijarro et al., "Solubilization of Active and Stable Receptors for Vasoactive Intestinal Peptide from Rat Liver," *Regulatory Peptides,* 25:37–50 (1989). Cronin et al., "Biological Activity of a Growth Hormone Releasing Factor Secreted By a Human Tumor," *Am. J. Physiol.,* 244 (Endocrinol Metab) E346–E353 (1983). Leong et al., "Enumeration of Lactotropes and Somatotropes in Cultured Male and Female Pituitary Cells: Evidence in Favor of a Mammosomatotrope Subpopulation," *Endocrinology,* 116:1371–1378 (1985). Munson, et al., "Ligand: a Versatile Computerized Approach For Characterization of Ligand-Binding Systems," *Anal. Biochem.,* 107:220–239 (1980). Wessel, et al., "A Method for the Quantitative Recovery of Protein in Dilute Solution in the Presence of Detergents and Lipids," *Anal. Biochem.,* 138:141–143 (1984). Bagnato et al., "Gonadotropin-Induced Expression of Receptors for Growth Hormone Releasing Factor in Cultured Granulosa Cells*," *Endocrinology,* 128, 2889–2894 (1991) (compositions studied by Bagnato et al show GHRH binding properties which are different from binding properties of pituitary tissues). All articles and other documents mentioned herein are incorporated by reference as if reproduced in full below.

While the foregoing studies have been helpful in developing a preliminary understanding of the behavior of the GHRH-R, there remains a need for a sensitive and reproducible assay for the GHRH-R, which will enable the further characterization of the GHRH-R leading to the purification and cloning of the GHRH-R. Such an assay must overcome the problems of nonspecific binding of GHRH and GHRH analogs, and the low abundundance of the GHRH-receptor. Iodination and purification of GHRH analogs with resultant high specific activity allows for the improvement of specific binding to crude anterior pituitary membranes.

Therefore it is a primary object of the present invention to develop a sensitive and reproducible assay for GHRH binding.

It is a further object of the present invention to develop reagents to specifically and unambiguously label the GHRH-receptor.

It is yet another object of the present invention to develop a GHRH-receptor purification scheme and to obtain a GHRH-R isolate of sufficient purity, or capable of being readily purified to a purity, which will allow for at least partial sequencing of GHRH-R.

Thus, it is a further object of the present invention to produce purified GHRH-R.

SUMMARY OF THE INVENTION

These and other objects of the present invention are accomplished through an improved GHRH binding assay leading to the characterization and isolation of a crude GHRH-R extract (isolate). GHRH-R is characterized through the use of radio-iodinated probes formed from GHRH analogs. The GHRH analogs (GHRH$_a$ or GHRH$_b$) and other analogs are iodinated in a preferred embodiment using solid phase iodobeads, and the monoiodinated material purified by reverse phase HPLC so as to be essentially carrier-free. Non-specific binding of GHRH analogs to glass and plasticware during delivery and dilution has been substantially eliminated by using organic solvents. In a preferred embodiment, fifty percent acetonitrile is used for dilution and delivery of GHRH analogs. GHRH and $GHRH_a$ specific binding to crude anterior pituitary membrane pellets is increased by addition of a pore-forming antibiotic. In a preferred embodiment, the antibiotic alamethicin (at approximately 0.05 mg/ml) is combined with homogenized anterior pituitary membrane pellets to increase GHRH specific binding.

GHRH analogs containing UV sensitive cross-linking groups (photoprobes or photoaffinity probes) have been prepared that demonstrate specific high affinity, GTP sensitive, cross-linking to the GHRH-receptor. Probes differ in both the location of the photosensitive group and the length of the spacer arm. Preferred photoprobes are formed by coupling of the GHRH analog [$His^1$, $Nle^{27}$]-GHRH-(1-32)-$NH_2$ to N-5-azido-2-nitrobenzoyloxysuccinimide (ANB-NOS), or to sulfosuccinimidyl-6-(4'-azido-2'-nitrophenylamino) hexanoate (sulfo-SANPAH or SANPAH), followed by iodination and purification. Preferably, coupling to the reagent ANB-NOS is targeted at the lysines at the 12 or 21 positions; the compound is subsequently iodinated on the tyrosine at the 10 position, and the product purified by reverse phase HPLC to form a photoprobe to be referred to as $^{125}I$-$GHRH_a$-ANB-NOS. In an alternate embodiment, the photoprobe $^{125}I$-$GHRH_a$-SANPAH is formed in a dimethylformamide solvent system by coupling of SANPAH targeted to the N-terminal histidine of $GHRH_a$, purification by reverse phase HPLC, iodination of the tyrosine at the 10 position of the $GHRH_a$, and repurification by HPLC.

It has been surprisingly discovered that, by use of the aforementioned photoaffinity probes, it is possible to produce a soluble complex of $GHRH_a$ bound to GHRH-R; the covalently cross-linked complex is readily soluble in a mild detergent solution, preferably containing a zwitterionic detergent compound capable of solubilizing proteins, such as 3-[(3-cholamidopropyl)-dimethyl-ammonio]-1-propane sulfonate (referred to as CHAPS, available from Pierce or from ICN Biomedicals, of Irvine, Calif.), and that most of the nonspecifically cross-linked contaminants are not soluble in the mild detergent solution. It was then discovered that non-crosslinked complexes were also solubilized under these conditions. Photocrosslinking was performed after solubilization and proved that the receptor (GHRH-R) and ligand (GHRH-probe) had formed a stable soluble complex. In a preferred embodiment, this enables the elimination of up to about 90% of the non-specifically bound GHRH by extraction with a CHAPS containing solution, and removal of free peptide with charcoal/dextran. This results in a greatly improved GHRH binding assay.

In a further embodiment, a partially purified GHRH isolate is obtained through affinity chromatography by attachment of a function to GHRH or a GHRH analog, which has an affinity for a compound immobilized on a support. In a preferred embodiment, biotinylated derivatives of $GHRH_a$ are bound to GHRH-R, solubilized, and then immobilized on a streptavidin column; it has been discovered that the bound GHRH/GHRH-R complex disassociates at pH 5.0 in a buffer, thus forming a partially purified GHRH-R isolate, capable of being used to determine the amino acid residue sequence of the GHRH-R, which in a preferred embodiment occurs after further purification of the GHRH-R isolate using SDS-PAGE to remove compounds, such as G-proteins, which would interfere with sequencing, and thereby forming purified GHRH-R.

DESCRIPTION OF THE DRAWINGS

FIG. 5 is a radiograph of an SDS gel of photoaffinity cross-linking as in FIG. 4, which includes the effects of GTP$\gamma$S and also partial deglycosylation with neuraminidase.

FIG. 7 demonstrates photoaffinity cross-linking of soluble complexes produced by following the experiment of FIG. 6 with ANB-NOS-GHRHa photoprobe, and the detergent soluble fraction was UV cross-linked after extraction. The leftmost two lanes were CHAPS extracted and the two lanes on the right were deoxycolate extracted.

FIG. 8 demonstrates the stability of CHAPS solubilized, charcoal dextran treated GHRHa-GHRH-R complexes that were exposed to 50 $\mu$M GTP$\gamma$S ($\pm$5 mM $Mg^{++}$), 10 nM DTT, or 1% Triton X-100 for 30 minutes and then charcoal dextran treated again to quantify the amount of dissociation.

DETAILED DESCRIPTION OF THE INVENTION

Figure 1:
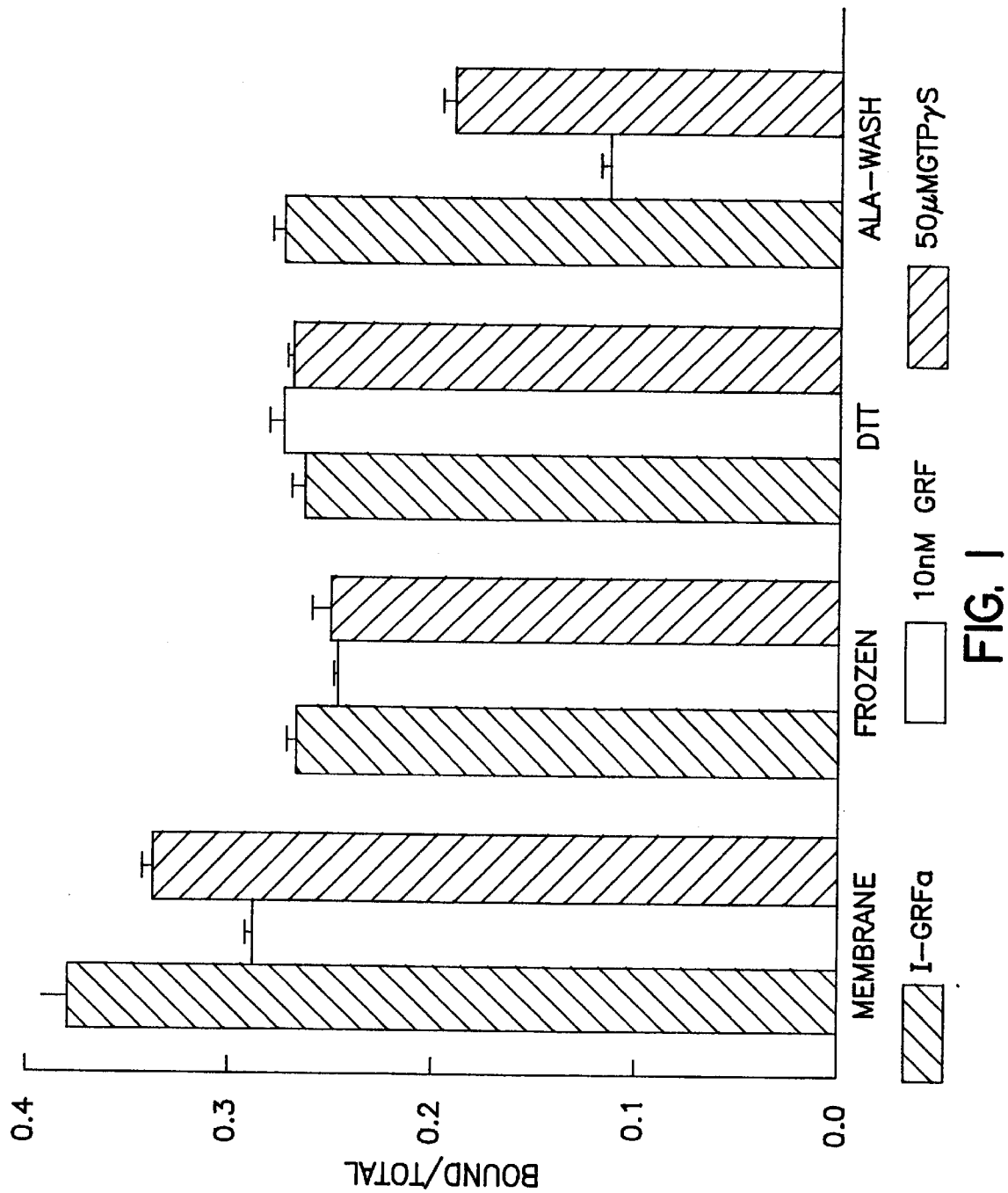
FIG. 1 is a bar chart demonstrating binding of 125I-$GHRH_a$ to crude ovine pituitary membrane pellets. The bars indicate the fraction of total counts bound to pellets after incubation with probe alone or in the presence of 10 nM GHRHa or 50 $\mu$M GTP$\gamma$S. Four different cases (sets of bars) are shown. The first case (membrane) shows binding to a preparation of crude membrane pellets. The second set (frozen) shows that there is little specific binding in the same membrane preparation after it has been frozen and thawed. The third set (DTT) shows binding to this same preparation (not frozen), but in the presence of 1 mM DTT. The fourth set (ala-wash) shows an improved protocol of the present invention which includes the pore forming antibiotic alamethicin and an additional wash step. Error bars indicate standard error of the mean, and N=3 or 4 replicates per point.

An overall approach to cloning of the GHRH-receptor involves (1) characterizing the GHRH-receptor, (2) using the knowledge of the characteristics of the GHRH-receptor to isolate the GHRH-receptor, (3) determining the peptide sequence of the GHRH-receptor (or a portion of the GHRH-receptor), (4) determining the DNA sequence which is responsible for the production of the GHRH-receptor by use of degenerate oligonucleotide sequences to screen a cDNA library, and (5) cloning of the DNA sequence.

Characterization of the GHRH-R

GHRH-Binding Assay.

In one aspect, the present invention is directed to a sensitive and reproducible assay for GHRH binding to the GHRH receptor, which demonstrates reversible high affinity GHRH-specific, GTP-dependent, binding. Because of the high nonspecific binding of the negatively charged GHRH peptide, use of a simpler filtration type binding assay has been impossible. With the assay of the present invention, specific binding (defined as the counts of gamma, $\gamma$, radiation produced by $^{125}$I-GHRH$_a$ binding which are eliminated from homogenized membrane pellets by 10 nM GHRHa) is 30 to 60% of the total counts bound in crude membrane pellets and up to 90% of the counts after extraction with a mild detergent (for example CHAPS) and charcoal/dextran treatment. A preferred embodiment of the binding assay of the present invention involves many factors, including a gentle solid-phase iodination protocol, HPLC purification of carrier free radioligand, an organic solvent system for the quantitative delivery of GHRHa, both plated cell and reverse hemolytic plaque assays to confirm the biological activity of the probe, and the use of about 0.05 mg/ml alamethicin, a pore forming antibiotic to increase specific radioligand binding to anterior pituitary membrane pellets. Alamethicin both increases specific binding and decreases trapped counts. A wash decreases recovered counts but further improves the relative amount of specific binding.

A preferred GHRH$_a$ analog for receptor binding studies is [His$^1$, Nle$^{27}$]-GHRH-(1-32)-NH$_2$ (referred to as GHRH$_a$). The GHRH analog is a peptide which has good GHRH-R binding activity, and differs from the human sequence in length, and has two amino acids, which are altered to facilitate its use as an iodination substrate. A prefered source of GHRHa is Peninsula Laboratories (Belmont, Calif.).

Preparation of iodinated GHRH analogs of optimal specific activity and biological activity is performed by first iodinating GHRH analogs (including photoprobes) using solid phase iodobeads (such as those available from Pierce), and then the monoiodinated material is purified essentially carrier-free by reverse phase HPLC, preferably using a fluorocarbon based Bio-Series Poly F column (available from MacMod). Quantitative dilution and delivery of GHRH analogs is obtained using organic solvents, preferably a 50% acetonitrile in water solution is used as a carrier. In this way, inaccurate and non-reproducible dilutions encountered with aqueous vehicles are avoided.

It has been surprisingly discovered that an approximately three-fold increase in specific binding, compared to prior methodology, is obtained when a pore-forming antibiotic is combined with crude anterior pituitary membrane pellets (See Struthers, et al., *Endocrinology*, 124:24 (1989). In a preferred embodiment, addition of about 50 $\mu$g/ml of the antibiotic alamethicin is utilized to obtain optimal specific binding.

With reference to FIG. 1, the binding of $^{125}$I-GHRH$_a$ probe to crude membrane pellets which have been treated under different conditions is presented. There are four sets of three bars. Each bar in a set indicates the fraction of total counts bound after incubation with iodinated probe. For each set of three bars, the left bar indicates total counts bound after incubation with iodinated probe alone, without pre-exposure of the membranes to cold GHRH or another compound known to compete with GHRH$_a$ or interfere with GHRH$_a$ binding. The center bar indicates the fraction of total counts bound after incubation with iodinated probe which has been added to the incubation together with 10 nM unlabeled GHRH$_a$ (which competes for specific binding sites). The difference between the leftmost and center bar of each set of bars indicates specific binding of GHRH, which represents the amount of GHRH-R present. The right hand bar indicates the fraction of total counts bound after incubation with $^{125}$I-probe in the presence of 50 $\mu$M GTP$\gamma$S. Since GTP$\gamma$S is known to cause dissociation of G-protein from some receptor complexes resulting in lowered affinity and decreased binding, the decrease in specific binding when using GTP$\gamma$S is consistent with the presence of GHRH-R-G-protein complex.

Specific binding is defined as the difference in the binding seen with 20 pM iodinated analog alone and binding of the analog in the presence of 10 nM non-iodinated GHRH$_a$. Saturation binding, Scatcherd analysis; competition studies, and other data discussed here show that these high affinity sites are specific binding sites.

Figure 2B:
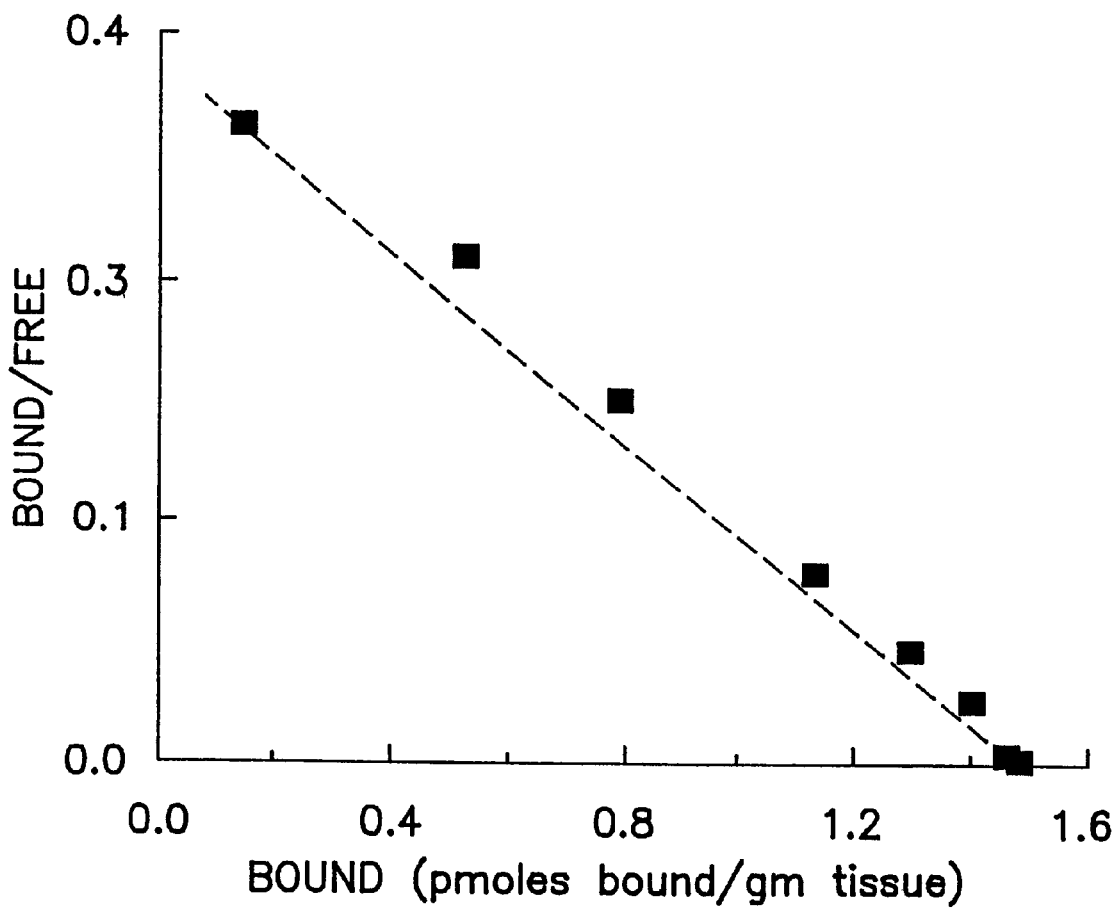
FIG. 2 is a graph used for saturation binding analysis. Points are data from binding assays performed in the presence of increasing levels of unlabeled GHRHa. Error bars indicate standard error of the mean. The inset shows plot of the same data and curve in the Scatchard coordinate system (error base not shown on inset).

With reference to FIG. 2, saturation binding studies demonstrate binding of the GHRH analogue [His$^1$, Nle$^{27}$]-GHRH-(1–32)-NH2 (GHRHa) to a single high affinity site with a Kd of about 160 pM. Some error bars were too small to show (N=6 replicates per point). This data was analyzed with the computer program Ligand, which determines binding constants based on a statistically weighted least squares fit to the ligand binding equation in a nontransformed coordinate system. The program reports a single binding site with a K$_d$=150±10 pM and R=1.5±0.09 pmoles/gm tissue (Best fit value=approximate SEM of fit). Statistical tests support this single binding site model. The dotted line is the theoretical curve generated using these constants in the binding equation.

Specific binding of GHRHa radioligand is reduced up to 65% by 50 $\mu$M GTP$\gamma$S. The related peptides VIP and PACAP did not compete for this binding site at 100 nanomolar concentrations. This binding represents a high affinity G-protein linked GHRH-R. It is known that VIP binding to the VIP receptor is sensitive to sulfhydryl reducing agents. Such specific binding in the GHRH assay is completely eliminated by preincubation with 1 mM dithiothreitol (DTT, which is known to prevent high affinity binding to related receptors), thus further supporting the conclusion that the GHRH-R receptor is the binding site.

Photoaffinity Probes

Photoaffinity probes were prepared using photoreactive cross-linking agents; these probes differ in both the location of the photosensitive group and the length of the spacer arm. The probes are capable of binding to GHRH-R in the absence of UV radiation and of cross-linking to GHRH-R under the influence of UV radiation. Preferred non-limiting examples of photoaffinity probes and methods for making same follow:

1) $^{125}$I-GHRHa-ANB-NOS

The 32 amino acid GHRH analogue [His$^1$, Nle$^{27}$]-GHRH-(1-32)-NH$_2$ (GHRHa) was coupled to the reagent N-5-azido-2-nitrobenzoyloxysuccinimide (ANB-NOS) targeted at lysine 12 or 21 to form GHRHa-ANB-NOS. The GHRHa-ANB-NOS was iodinated using iodobeads to form the radioligand ("photoprobe") $^{125}$I-GHRHa-ANB-NOS ("hot GHRHa-ANB-NOS" or "hot photoprobe") (preferred iodobeads are available from Pierce, Rockford, Ill.).

2) I-GHRHa-SANPAH

In a dimethylformamide solvent system, the GHRH analog [His$^1$, Nle$^{27}$]-GHRH-(1-32)-NH$_2$ to N-5-azido-2-nitrobenzoyloxysuccinimide (ANB-NOS), was coupled to sulfosuccinimidyl-6-(4'-azido-2'-nitrophenylamino) hexanoate (sulfo-SANPAH or SANPAH) targeting at the N-terminal histidine of GHRHa. The radioiodinated material was then purified essentially free of starting peptide by reverse phase HPLC on a fluorocarbon based Bio Series Poly F Column (available from Mac-Mod Analytical, Chadds Ford, Pa.) using a shallow gradient of acetonitrile.

Figure 3:
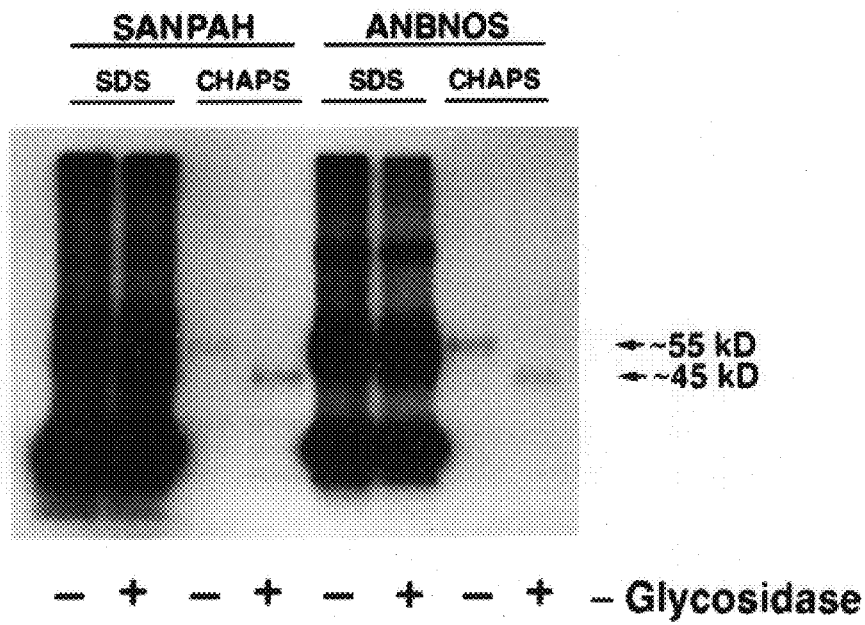
FIG. 3 is a radiograph of an SDS gel which demonstrates photoaffinity cross-linking of receptor. Cross-linking to crude ovine pituitary membranes is demonstrated with two different photoprobes (SANPAH and ANS-NOS), each extracted by two different methods (SDS and CHAPS). The effect of deglycosylating enzymes is also shown in each case. CHAPS extracts show greatly reduced nonspecific binding. Both photoprobes label a 55 kDa band that shifts to 45 kDa upon deglycosylation.
Figure 4:
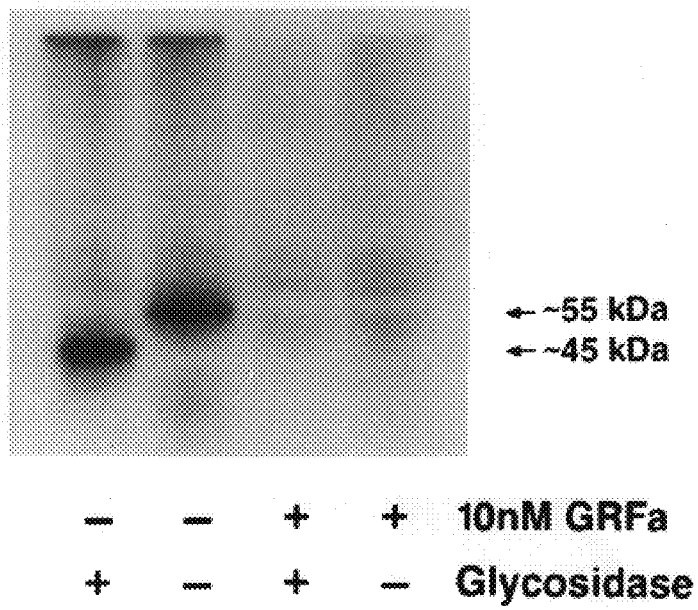
FIG. 4 is a radiograph of an SDS gel as in FIG. 3 showing CHAPS extracted ANB-NOS cross-linking which demonstrates competition by 10 nM GHRH and also shows deglycosylation.

Photoprobe binding in ovine pituitary membrane pellets was determined by γ-counting and UV induced cross-linking was examined by autoradiagraphy of sodium dodecylsulfate polyacrylamide electrophoresis (SDS-PAGE) gels. $^{125}$I-GHRH$_a$-ANB-NOS probe bound with an affinity of about one nanomole, nM (compared to about 160 picomole, pM, for GHRH$_a$). SDS-PAGE revealed a band at about 55 kDa for ovine pituitary (in bovine pituitary, 57 kDa), which was completely eliminated in the presence of 10 nM GHRH$_a$; this band was reduced over 50% by 50 μM GTPγS, and was unaffected by 100 nM VIP. Thus, the 55 kDa band is due to photocrosslinking of the GHRH-R. FIG. 3 shows that this specific 55 kDa band is separated from most nonspecifically cross-linked material by CHAPS extraction. FIG. 4 demonstrates competition with 10 nM GHRHa. FIG. 5 demonstrates the effect of GTPγS on cross-linking.

Treatment of the cross-linked GHRH-receptor with neuraminidase caused the 55 kDa band to shift to 50 kDa, which is attributed to the removal of charged terminal sialic acid groups which decrease mobility in the gel (FIG. 5). Treatment of the cross-linked GHRH-receptor with a purified, protease-free mixture of endoglycosidase F and N-glycosidase F (available from Boehringer Mannheim of Indianapolis, Ind.) caused a shift in gel mobility to form a band at 45 kDa (shown in FIGS. 3 and 4); this indicates that the GHRH-receptor is an N-linked glycoprotein (common among G protein-linked receptors) and suggests the size of the deglycosylated protein chain. This size is consistent with the structure of VIP and secretin receptors.

Tests with immobilized lectins showed no binding of the cross-linked GHRH-receptor to wheat germ agglutinin, ricin, Limulus agglutinin, or concanavalin A. This makes the receptor unusual and offers an approach to the purification and isolation of this receptor from other receptors which do bind to these lectins. Following neuraminidase and β-galactosidase treatment, the receptor bound specifically to peanut agglutinin, providing an additional approach to separation and purification of the GHRH receptor.

Soluble GHRH-GHRH-R Complex and Improved Binding Assay

Photoaffinity cross-linking showed that the covalently coupled receptor-ligand complexes are soluble in a mild detergent solution, preferably a solution containing CHAPS. Preincubating GHRH with the receptor, using the conditions of the aforementioned membrane binding assay, allowed CHAPS extraction and solubilization of an intact receptor-ligand complex even when not cross-linked. This complex was detected by gamma counting after detergent extraction of membranes incubated with $^{125}$I-GHRHa ("hot" GHRHa) without crosslinking.

Figure 6:
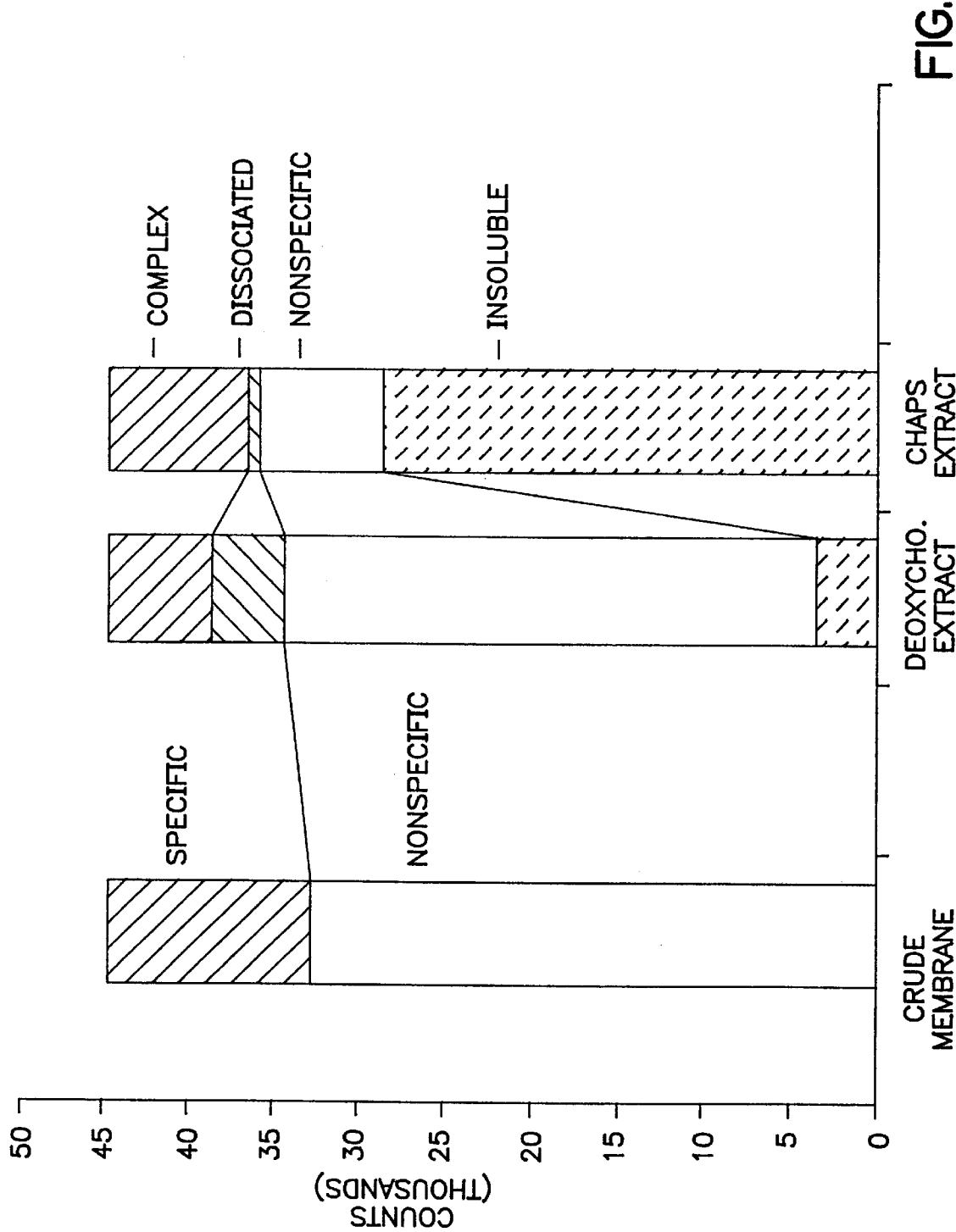
FIG. 6 demonstrates the solubility of GHRHa-GHRH-R complexes which were prepared by allowing radioiodinated GHRHa to bind to crude ovine pituitary membranes, in either the presence or absence of 10 nM unlabeled GHRHa.

FIG. 6 shows that most of the specific counts seen in the crude membrane were CHAPS extracted as a specific complex associated with receptor. The data for FIG. 6 was obtained as follows. Radioiodinated GHRHa was allowed to bind to crude ovine pituitary membranes either in the presence or absence of 10 nM unlabeled GHRHa. This was followed by detergent extraction and centrifugation; the supernatants were then charcoal/dextran treated to separate protein bound from free GHRHa, and the radioiodine in each fraction was counted. The labled GHRHa bound in the crude membrane could thus be followed upon detergent treatment and characterized as: (1) insoluble, (2) soluble and nonspecifically bound, (3) specifically bound but detergent dissociated, or (4) soluble and specifically bound. As known from photocross-linking, most of the nonspecifically bound counts were not CHAPS soluble. Extraction with a deoxycholate detergent mix solubilized slightly more total counts, but much of this was unstable and dissociated, and nonspecific counts predominated.

FIG. 7 shows the results of this photocross-linking to confirm that this complex contained receptor. The membranes were prebound with photoprobe ($^{125}$I-ANB-NOS-GHRHa) in the dark, CHAPS extracted, and then cross-linked with UV. This proves that the GHRH was still bound to the solubilized receptor. In the CHAPS extract, most of the binding was in the 55 kD receptor band while in the deoxycholate case most of the bands were nonspecific. This matches well with the binding studies shown in FIG. 6 (though photoprobes have higher nonspecific binding), and demonstrates that the specific binding of the GHRH analog in the soluble complexes is to the 55 kDa receptor. Consistent with FIG. 6, the complex was much more stable in CHAPS than deoxycholate. There were also few nonspecific bands (One is just below the 55 kDa receptor band) upon photocross-linking of the CHAPS extract.

FIG. 8 demonstrates that CHAPS extraction amounts to an improved binding assay with greatly reduced nonspecific counts and increased sensitivity (Compare to FIG. 1). This figure also shows that the complex is partially dissociated by 50 μM GTPγS suggesting that G proteins are still associated with the complex solubilized in a detergent solution containing CHAPS. FIG. 1 shows that 1 mM DTT prevented specific binding before GHRH when added. FIG. 8 shows only a partial effect from 20 mM DTT after prebinding has occurred. This complex was also quite stable in up to 1M NaCl overnight at 4° C., but was completely dissociated by 1% triton X-100 (surfactant). Note the low background obtained when using CHAPS soluble, charcoal dextran treated samples for a binding assay.

Figure 9:
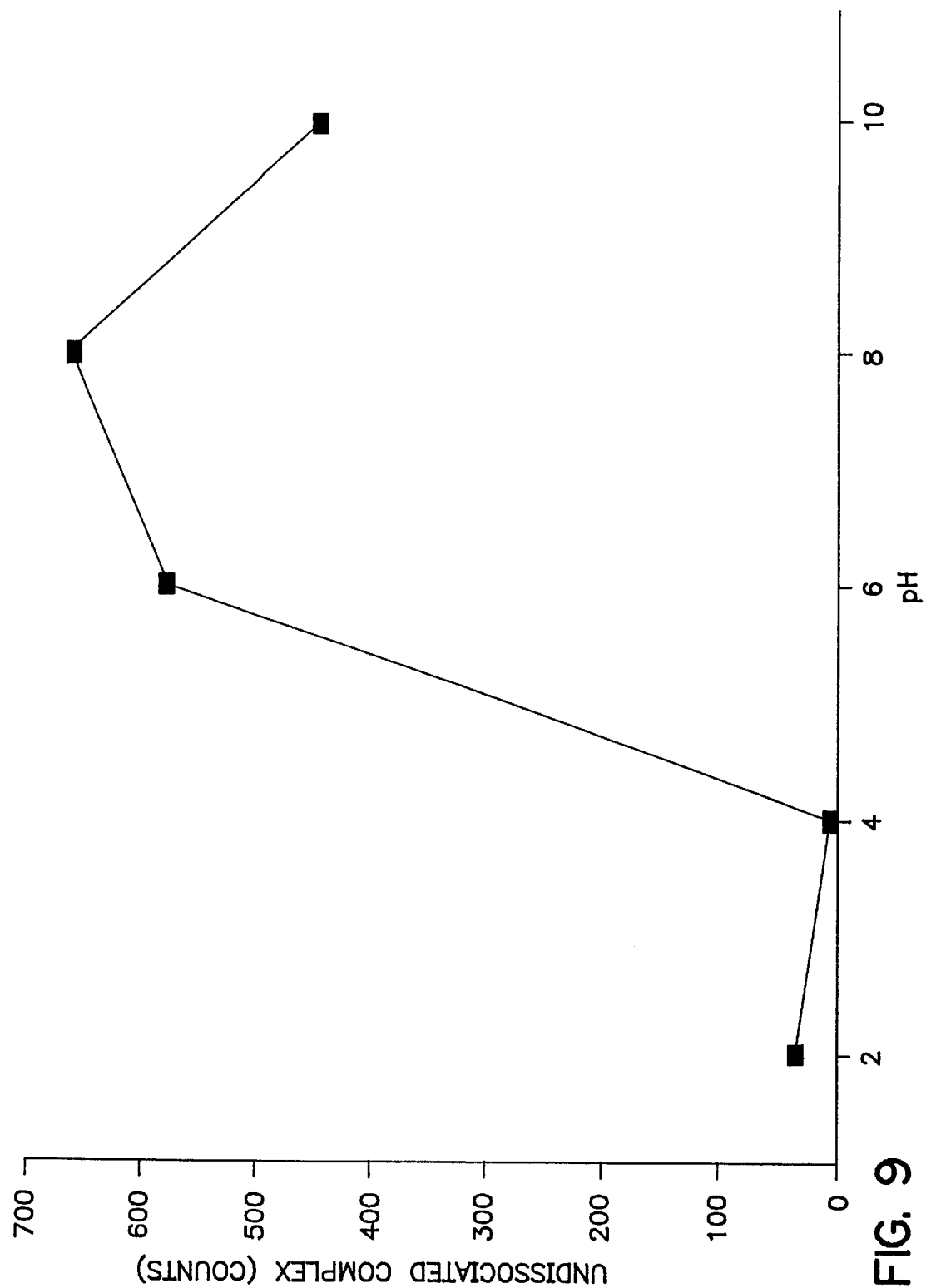
FIG. 9 demonstrates dissociation of soluble GHRH-GHRH-R complexes at low pH with stability of soluble specific complexes at varying pH evaluated as in FIG. 8. Further data indicates that near complete dissociation is obtained at pH 5 or below.

The pH stability of the soluble receptor-ligand complex is shown in FIG. 9. There is a sharp transition with the complex unstable at pH 5.5 and below, stable and able to exchange the bound GHRH with free GHRH between pH 5.5 and 6, and very stable and nonexchangable at pH 7. The stability of this complex gives us both an improved GHRH-R binding assay, and the basis for a new receptor purification methodology.

Isolation and Purifacation of GHRH-R

Biotinylated GHRH analogs were developed with the aim of purifying the GHRH receptor as a receptor-ligand complex that can be retained on immobilized streptavidin. The first analog tested was [His1, Nle27]-GHRH-(1-32)-NH$_2$ (GHRHa) biotinylated at lysines at the 12 and/or 21 positions using the N-hydroxysuccinimide reagent NHS-LC-Biotin (available from Pierce). This analog was iodinated at the tyrosine at the 10 position and resolved as mono and dibiotinylated forms on HPLC. Greater than 90% of these products bound to immobilized streptavidin within 30 minutes. The monobiotinylated GHRHa had two-fold reduced receptor binding affinity compared to GHRHa while the dibiotinylated had near zero activity. The biotin group appears to be in the receptor's binding pocket, as binding to streptavidin blocked binding to the receptor. The next analog tested was [His1, Nle27, Cys33]-GHRH-(1-33)-NH$_2$. It has a strong tendency to dimerize and none of the species that could displace GHRHa in a competition binding assay were biotinylated.

It has been surprisingly discovered that [His1, Nle27, Biotin-Lys41]-GHRH-(1-41)-NH$_2$ (referred to herein as GHRHb) binds the receptor with an affinity comparable to GHRHa (a preferred source for preparing GHRHb is Nuros Corporation of San Jose, Calif.). To prove that this analog could be used in receptor purification, it was iodinated, a photosensitive cross-linking group (ANB-NOS) incorporated, and the compound purified by HPLC. This iodo-biotinyl-photoactivatable GHRH, $^{125}$I-GHRHb-ANB-NOS, was bound to receptors in crude bovine pituitary membranes. The receptor-ligand complexes were CHAPS solublized, charcoal dextran stripped to remove free GHRH and bound to immobilized streptavidin.

To test if the streptavidin dislodged the receptor from the complex, samples were UV cross-linked before and after streptavidin binding and analyzed by autoradiography. This demonstrated that a significant fraction (30%) of the receptor that was available for binding could be retained on streptavidin beads. Studies of soluble receptor-ligand complex stability (see FIG. 9) indicate that a high salt (0.5M NaCl) wash of the streptavidin beads followed by a low pH elution (pH 5) (preferably using a phosphate, acetate, citrate or other suitable buffer solution) results in significant receptor purification to produce a GHRH-R isolate. The GHRH-R isolate obtained is of sufficient purity to allow for sequencing of the GHRH-R; in a preferred embodiment G-proteins and other interfering contaminants are removed, by methods, such as but not limited to gel electrophoresis in order to obtain GHRH-R of at least sufficient purity to perform sequencing.

Figure 10:
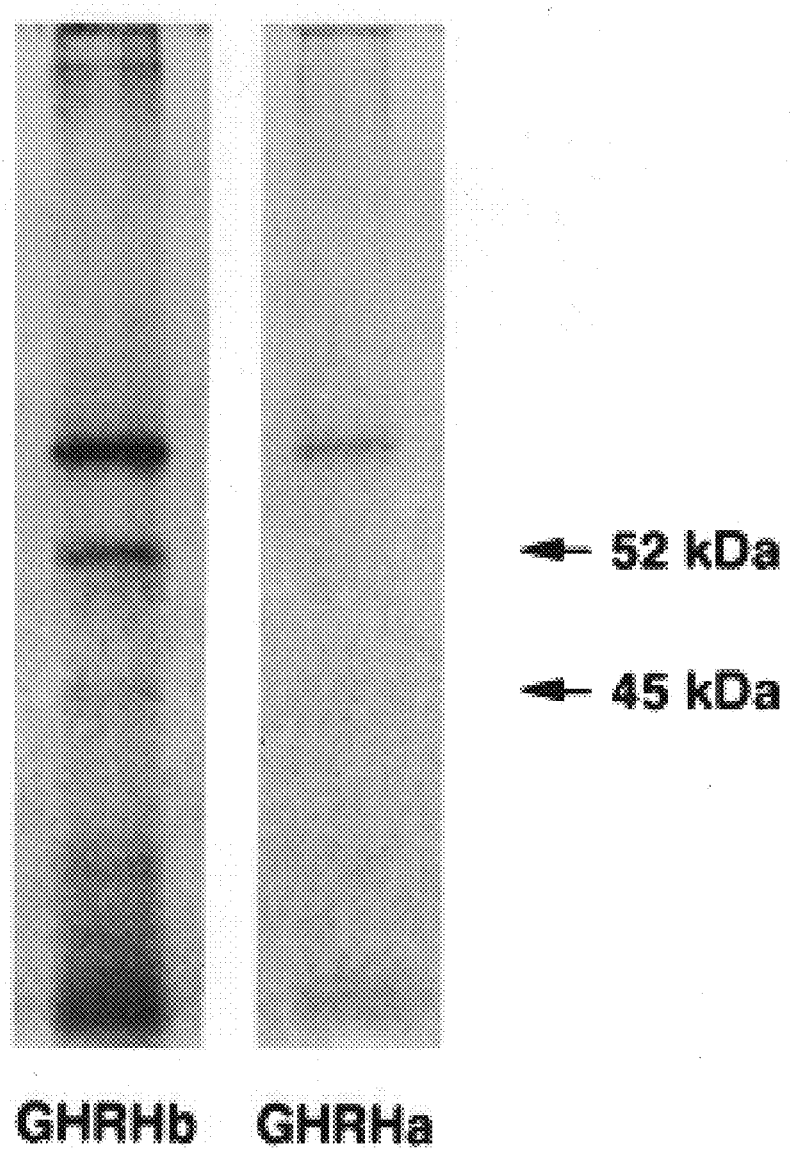
FIG. 10 demonstrates SDS-PAGE analysis of the eluate, containing purified GHRH-R, obtained from affinity chromatography of the biotinylated receptor complex GHRHb-GHRH-R on a streptavidin agarose column.

FIG. 10 demonstrates the results of affinity purification of the biotinylated receptor complex (GHRHb-GHRH-R) on a streptavidin agarose column. The agarose beads, having the bound complex, were washed in 0.5 m NaCl to minimize nonspecific binding and then the receptor was dissociated from the biotinylated ligand at pH 5.0, and eluted from the column. The eluate was concentrated by centrifuge-driven ultrafiltration, and analyzed by SDS-PAGE. A control column was run in parallel and treated identically except that the soluble receptor complexes were prebound with the nonbiotinylated analog GHRHa. The GHRHb lane on this silver stained gel shows bands at 52 and 45 kDa that are not seen in the GHRHa lane. The 52 kDa band corresponds to the size expected for the receptor because the 55 kDa band seen in crosslinking studies includes the covalently attached 3.6 kDa GHRHa peptide. The 45 kDa band is the size reported for the stimulator G-protein G$_s$ which is thought to be a subunit of the GHRH receptor complex. The coelution of these two bands and their absence in the control column confirms that highly purified GHRH-R has been prepared.

Experimental Methods and Examples

The following non-limiting examples further demonstrate the improved GHRH binding assay of the present invention, and method of purifying the GHRH-receptor based on solubilization of an intact GHRH/GHRH-receptor complex. It is to be understood that a wide variety of other materials than those specifically mentioned herein may be used to practice the invention without undue experimentation.

1. Binding Assay in Crude Membrane Pellets

Tissue Preparation

All steps were performed at 4° C. Frozen ovine or bovine anterior pituitaries (ovine: approximately 1 gm/pituitary obtained from Dr. Iain Clarke, Melbourne, Australia; bovine: approximately 2.5 gm/pituitary special handling from Pel-Freez, of Rogers, Ak.) were washed of blood, cleaned of connective tissue and homogenized (using a Dounce homogenizer) in 50 mM HEPES buffer, 100 mM NaCl, 10 mM EDTA, 0.1 $\mu$M EGTA, pH 7.4 with 0.5 mM PMSF (phenyl methyl sulfonyl fluoride), 10 $\mu$g/ml leupeptin, 10 $\mu$g/ml pepstatin A, and 200 U/ml (units/ml) aprotinin. This buffer is used to remove endogenous GTP which might be bound to G proteins and to restore high affinity binding. The homogenate was spun at top speed in a microfuge and the supernatant discarded. The upper (membrane) layer of the pellet was then gently resuspended in binding buffer containing 50 mM Tris buffer, 5 mM EGTA, 5 mM MgCl$_2$, 50 $\mu$g/ml alamethicin, 30 $\mu$g/ml bacitracin and other protease inhibitors as above.

Binding Conditions and Analysis $\frac{1}{50}$ pituitary equivalent per tube was incubated in binding buffer with approximately 100,000 counts of iodinated probe in a volume of 500 $\mu$l at room temperature for 1 hour. The total counts delivered and the percent of counts bound for each tube was determined with 3 to 6 replicates per experimental condition. Saturation binding profiles were analyzed with the computer program Ligand which performs a statistically weighted least squares fit to the exact ligand binding equation in nontransformed coordinates. Statistical measures (F test and runs test) indicated a convincingly good fit to a single binding site model. A representative saturation binding analysis is presented in FIG. 2.

Results

Treatment of the tissue with 10 mM EDTA was essential to allow the removal of endogonous GTP and reveal the high affinity GTP dependant sites. Initially, nonspecific binding was overwhelming and a wide variety of blocking agents offered no improvement. Slightly better binding signals were seen in membrane fractions purified by sucrose density centrifugation. To obtain consistent results, large batches of crude membrane were prepared from frozen pituitaries and aliquots of this membrane were frozen for later assay. With reference to FIG. 1, a great increase in specific binding was noted when the membranes were tested directly after homogenation. One possible mechanism for this freeze-thaw effect is the formation of vesicles which interfere with the assay. In testing this possibility, it was found that the pore forming antibiotic alamethicin (50 ug/ml) increased the ratio of specific binding/total binding 3 fold, as is graphically illustrated in FIG. 1. Most of this increase was due to a drop in nonspecific binding, possibly due to the release of probe trapped in vesicles. An additional wash of the membrane pellets by centrifugation was included to maximize the enhancement of specific over nonspecific binding despite the loss in total counts recovered.

Computer analysis of saturation binding studies with the program Ligand indicates a single binding site with a Kd=158 ±13 pM and that the total number of specific binding sites (RT) is 1.5±0.09 pmoles/gm tisse (best fit value±approximate standard error of means (SEM). Since the affinity for GHRHa is commensurate with GHRHa's biological potency, and because of specificity for GHRH over related peptides (no competition by 100 nM VIP or PACAP) and sensitivity to 50 uM GTP$\gamma$S and to 1.0 mM DTT, this binding indicates the presence of GHRH-R.

Comparison of the $^{125}$I-GHRHa to a commercially available iodinated human GHRH (Amerisham, Arlington Heights, Ill.) showed much similarity; $^{125}$I-GHRH$_a$ displayed a slightly better specific binding and a somewhat stronger GTP effect.

Evaluation of Photoaffinity Probe Binding

Two different photoaffinity probes were prepared using heterobifunctional photoreactive cross-linking agents available from Pierce as discussed above (Rockford, Ill.). SANPAH was coupled to GHRHa targeted at the N-terminal histidine using a DMF solvent system. ANB-NOS was coupled to GHRHa targeted at lysines 12 or 21. Each coupling group-GHRHa product was purified by HPLC, iodinated and repurified.

Photoprobe binding to membranes was evaluated with crude membrane binding assay and then analyzed further by SDS-PAGE electrophoresis to identify the binding sites. Photoprobes were incubated in the dark, photolysed for 10 minutes with a long wave (366 nm) UV lamp, and then the samples were pelleted. The pellets were counted and then extracted by boiling directly in SDS sample buffer (total SDS extracts). Alternatively, the labeled pellets were extracted in a mild detergent solution (5 mM CHAPS) centrifuged, and the chloroform/methanol concentrated supernatants denatured with SDS buffer (CHAPS extracts). These samples were then electrophoresed in SDS gels and autoradiographed.

Results

Binding assay revealed that both photoprobes bound to membrane pellets, and could be totally displaced by 10 nM GHRHa, or partially displaced by 50 $\mu$M GTP$\gamma$S. Both gave greater nonspecific binding than I-GHRHa. Gels of total SDS extracts of the affinity cross-linked pellets displayed this nonspecific binding as bands unaffected by GHRHa or GTP$\gamma$S. These nonspecific bands differed somewhat from run to run and between the two probes (FIG. 3). The nonionic detergent CHAPS is a weak solubilizer of proteins; receptor purification work demonstrated the ability of solutions containing CHAPS to solubilize GHRH binding activity. When extracts of cross-linked pellets obtained by using a solution containing 5mM CHAPS were examined on SDS gels, visualization of receptor cross-linking was much improved, as most of the nonspecifically labeled protein was not solubilized. With reference to FIGS. 3 and 4, a 55 kD band, whose labeling is greatly effected by GHRHa or GTP$\gamma$S, is clearly visible with both probes, and represents the GHRH-R. These photoprobes are invaluable in the further characterization, purification and cloning of the GHRH-receptor.

Deglycosylation

Since the extracellular portion of most G protein-linked membrane receptors is known to contain multiple carbohydrate groups covalently linked to arginine residues (N-linked), experiments were performed to confirm that the specifically photolabeled band in FIGS. 3 and 4 is an N-linked glycoprotein. Samples were treated with a purified, protease-free mixture of endoglycosidase F and N-glycosidase F.

Photolabeled pellets (extracted using SDS or CHAPS) were boiled in SDS sample buffer, diluted, and incubated overnight at 37° C. with 1.25% Nonidet P-40 (a non-ionic detergent also known as NP-40) in either 0.5 units of glycosidase or blank. These samples were then concentrated by a chloroform-methanol precipitation protocol (see Wessel, et al., Anal. Biochem., 138:141–143 (1984)) and electrophoresed on SDS gels.

With reference to FIGS. 3 and 4, it can be seen that the mobility of the specifically photolabeled band shifts from approximately 55 kD to approximately 45 kD only in the presence of glycosidase. Other bands, visible in the SDS extracted samples, and judged to be nonspecifically labeled by the lack of response to GHRH$_a$ or GTP$\gamma$S, are not deglycosylated. This is the first proof that the GHRH-R is a glycoprotein, and provides the best estimate of the true size of the protein chain. As is shown in FIG. 5, treatment of the photolabeled receptor with neuraminidase caused a shift in gel mobility to approximately 52 kD. This demonstrates that the receptor has a number of terminal sialic acid groups on its oligosaccharide chains. These sialic acid groups also affect the receptor's pI, as seen on isoelectric focusing gels, hydrophobicity on HPLC, and also its lectin binding properties. Deglycosylation is useful in purification strategies and in facilitating proteolytic cleavage of the receptor for sequencing.

Solubilization of Receptor-GHRH Complexes

Pituitary membrane preparations solubilized in solutions containing CHAPS showed only GTP insensitive low affinity sites (Kd approximately 500 nM), as measured with a charcoaldextran binding assay (adapted from that developed for VIP by Paul, et al., J. Biol. Chem., 262:158–162 (1987)). Other detergents preserved even less binding, which indicates that the GHRH-R was not stable to these treatments. Photoaffinity cross-linking results revealed that the covalently coupled receptor-ligand complex is soluble in a solution containing CHAPS. Preincubating GHRH with the receptor using the conditions of the membrane binding assay of the present invention, followed by extraction with a mild detergent solution, preferably containing CHAPS, revealed solubilization of an intact receptor-ligand complex. This soluble complex was detected by detergent extraction of membranes incubated with $^{125}$I-GHRH analog, or $^{125}$I-GHRH analog following treatment with 10 nM cold GHRH.

Purified GHRH-R

Biotinylated GHRH analog was then utilized to form a soluble GHRH$_b$-GHRH-R complex, and this soluble complex, following extraction using CHAPS, and purification with charcoal-dextran, was run over a streptavidin column. The streptavidin column was then washed with a NaCl solution, and subsequently a buffer solution having a pH of 5.0 was run over the column in order to produce a GHRH-R isolate.

The GHRH-R isolate can then be further purified by SDS-PAGE. A band appearing at about 52 KDa (corresponding to pure GHRH-R) can be blotted with a standard PVDF membrane. The PVDF membrane having purified GHRH-R theron can then be digested on the membrane and sequenced to obtain the complete or partial amino acid residue sequence of the GHRH-R following conventional sequencing methods.

The amino acid residue sequence or sequences obtained from the sequencing step can then be utilized as a basis for forming degenerate probes for use in cloning of the gene responsible for production of GHRH-R.

Thus, an improved methodology for measuring binding of GHRH analogs to the GHRH receptor in ovine and bovine pituitary membranes has been disclosed (including methods for iodination, purification and delivery of GHRH analogs, and the use of pore forming antibiotics). This led to the development of methods for the GTP sensitive, GHRH specific, high affinity photo-labeling of the GHRH receptor. Such labelling of this receptor was not previously accomplished. This allowed for the characterization of the receptor's size, glycosylation, solubility and other properties. This led to the discovery that a mild detergent solution, including compounds such as CHAPS, could extract the bound GHRH-GHRH-receptor complex in a stable, soluble form. CHAPS extraction and charcoal/dextran treatment (to bind free GHRH) gives a soluble receptor-ligand complex that is purified from most nonspecific GHRH binding, and thus is very useful as a new, low background GHRH binding assay with better sensitivity than previously possible, and also as a starting point for receptor purification. This receptor-ligand complex is relatively stable to salt washes, GHRH exchange and GTP or DTT treatment, but not to lowered pH. A C-terminally biotinylated GHRH analog has been invented that, when bound in a soluble GHRH-R complex, allows for the purification of GHRH receptor by retention on a column of immobilized streptavidin, followed by a salt wash, and pH 5 elution. This purified receptor protein is suitable for partial sequencing of receptor peptides and this sequence information is valuable for the cloning of the GHRH receptor cDNA.

From the above teachings, it is apparent that many modifications and variations of the present invention are possible. By way of non-limiting example, it is contemplated that other complexes of GHRH-R in crude pituitary samples can be bound to affinity columns in order to produce purified GHRH-R. It is therefore to be understood that the invention may be practiced otherwise than as specifically described.

We claim:

1. An isolated purified growth hormone releasing hormone receptor having a molecular weight determined by SDS-PAGE under reducing conditions of about 55 kDa.

2. The growth hormone releasing hormone receptor of claim 1, said receptor exhibiting a deglycosylation pattern upon treatment with neuraminidase of cleaving sialic acid.

3. An isolated, purified growth hormone releasing hormone receptor having a molecular weight determined by SDS-PAGE under reducing conditions of about 55 kDa and being produced by a method comprising immobilizing complexed growth hormone releasing hormone receptor on an affinity chromatography support, and subsequent disassociation of said complex on said support to produce an isolated, purified growth hormone releasing hormone receptor.

4. The growth hormone releasing hormone receptor of claim 3, said receptor exhibiting a deglycosylation pattern upon treatment with neuraminidase of cleaving sialic acid.

5. An isolated, purified growth hormone releasing hormone receptor having a molecular weight determined by SDS-PAGE under reducing conditions of about 55 kDa and being produced by a method comprising solubilizing growth hormone releasing hormone receptor complexed with a growth hormone releasing hormone or a growth hormone releasing hormone analog in a mild detergent solution; immobilizing said complex on an affinity chromatography support; and subsequent disassociation of said complex on said support by lowering the pH to produce an isolated, purified growth hormone releasing hormone receptor.

6. The growth hormone releasing hormone receptor of claim 5, said receptor exhibiting a deglycosylation pattern upon treatment with neuraminidase of cleaving sialic acid.

7. The isolated, purified growth hormone releasing hormone receptor of claim 5, wherein said growth hormone releasing hormone analog is capable of binding to an affinity chromatography support.

8. The isolated, purified growth hormone releasing hormone receptor of claim 7, wherein said growth hormone releasing hormone analog is biotinylated.

9. The isolated, purified growth hormone releasing hormone receptor of claim 8, wherein said affinity chromatography support includes streptavidin functionalities capable of binding said biotinylated analog.

\* \* \* \* \*